United States Patent
Walther et al.

(10) Patent No.: US 6,346,245 B1
(45) Date of Patent: Feb. 12, 2002

(54) PROCEDURE FOR EXTRACTION AND USE OF HATCHING FLUID FROM ATLANTIC SALMON

(75) Inventors: Bernt Th. Walther; Chunjun J. Rong, both of Bergen (NO)

(73) Assignee: Aqua Bio Technology AS, Eikelandsosen (NO)

( * ) Notice: Subject to any disclaimer, the term of this patent is extended or adjusted under 35 U.S.C. 154(b) by 0 days.

(21) Appl. No.: 09/581,026

(22) PCT Filed: Dec. 11, 1998

(86) PCT No.: PCT/NO98/00378

§ 371 Date: Jun. 8, 2000

§ 102(e) Date: Jun. 8, 2000

(87) PCT Pub. No.: WO99/29836

PCT Pub. Date: Jun. 17, 1999

(30) Foreign Application Priority Data

Dec. 11, 1997 (NO) .......................................... 19975826

(51) Int. Cl.[7] .................. A61K 38/46; A61K 38/48; C07K 1/00; C12N 9/50; C12N 9/64
(52) U.S. Cl. ................ 424/94.63; 424/94.1; 424/94.63; 424/94.64; 424/94.65; 424/94.67; 435/219; 435/226; 530/324; 530/412; 530/413; 530/416; 530/417
(58) Field of Search .............................. 424/94.1, 94.65, 424/94.67, 94.63, 94.64; 530/324, 412, 413, 416, 417; 435/219, 226

(56) References Cited

FOREIGN PATENT DOCUMENTS

EP 0 292 663 * 11/1988

OTHER PUBLICATIONS

Kunert, Mycoses, (1992) 35(11–12):343–348.*
Harris and Angal, Protein Purification Methods: A Practical Approach. N.Y., Oxford University Press, 1989. p. 57–64, 151–161.*
Choko Kawabata et al., "Miltpain, New Cysteine Proteinase From the Milt of Chum Salmon", *Comp. Biochem. Physiol.,* vol. 117B, No. 3, 1997 p. 445–452.
F. Lahnsteiner et al., "Composition of the Ovarian Fluid in 4 Salmonid Species: Oncorhynchus Mykiss, Salmo Trutta f Lacustris, Salvelinus Alpinus and Hucho Hucho", *Reprod Nutr Dev,* vol. 35, 1995, p. 465–474.
Z. Luberda et al., "Catalytic Properties of Hatching Enzyme of Several Salmonid Species", *Arch. Hydrobiol.,* vol. 131, No. 4, Oct. 1994, p. 503–511.
C. J. Rong et al., "Endoproteolytic Hatching Enzyme From Atlantic Salmon (Salmo Salar) Embryos", University, Tromsoe, Norway, p. 127, 1994 Dialog Information Services, File 44, *Aquatic Sci & Fish Abs* No. 3627748.

* cited by examiner

*Primary Examiner*—Christopher S. F. Low
*Assistant Examiner*—Chih-Min Kam
(74) *Attorney, Agent, or Firm*—Young & Thompson

(57) ABSTRACT

A procedure is described for obtaining valuable endoproteases (or zonases) from hatchery-produced Atlantic salmon eggs. Synchronized hatching by for instance elevated temperature, is followed by filtration through cheese cloth. The filtrate (hatching fluid) may be stored for months or year (depending on conditions) without loss of activity. Extraneous matters are removed by centrifugation (16,000 g, 2×15 min) after addition of urea (2 or 4 M, or more). High purity zonases are obtained by simple chromatographic procedures (gel filtration, affinity chromatography, isoelectric focusing), yielding sequence-grade purity after all three steps are performed in sequence. All preparations of salmon zonases exhibit valuable enzymatic properties with regard to proteolysis, both in terms of catalysis and stability.

1 Claim, No Drawings

PROCEDURE FOR EXTRACTION AND USE OF HATCHING FLUID FROM ATLANTIC SALMON

CROSS REFERENCE TO RELATED APPLICATION

This is the 35 USC 371 national stage of international application PCT/NO98/00378, filed on Dec. 11, 1998, which designated the United States of America.

The present invention concerns a procedure for extracting endoproteolytic hatching enzymes (zonases) in waste water from hatcheries producing Atlantic salmon larvae, and in addition, it establishes a simple procedure for obtaining up to sequence-grade purity of these special endoproteases, which turn out to possess rather unique proteolytic characteristics.

Proteases in purified states are increasingly used in research, in laboratory and clinical analysis, and in food production procedures. Demand is increasing, especially for enzymes with properties commensurate with specific applications. This has stimulated quests for new sources of proteases which allow safe, sustainable and economical modes of production.

Here we exploit a new, rich source of endoproteases connected to aquaculture of Atlantic salmon. An essential aspect of this industry is the hatchery-production of developing eggs, which hatch to yield larvae. Hatching is accomplished by embryos producing endoproteases, which, when secreted, effectively and specifically split the eggshell open to allow the larva to swim out and start life on its own (Refs.: Yamagami 1988; Walther 1993).

The critical enzymes behind fish hatching have only been characterized in a few fishes, and in almost all cases, these zonases have been interpreted to be metallo-proteases (Refs.: Hagenmaier 1974; Ohzu & Kasuya 1979; Schoots & Denucé 1981; DiMichele et al. 1981; Yasumasu et al. 1989a, b; Araki & Onozato 1990; Hung et al. 1997). Gene structure of some zonase-type enzymes has only recently become available (Ref.: Yasumasu et al 1992).

Putative hatching enzymes have also been reported in invertebrates, where again most such enzymes have been interpreted as being metalloproteases (e.g. Barrett & Edward 1976; Lepage & Gache 1989; Roe & Lennarz 1990). However, a few strong cases for serine protease-like zonases have been reported (e.g. Post et al. 1988). Conversely, among higher vertebrates than fish, putative hatching enzymes have also been reported. For instance, both Urch & Hedrick (1981; concerning amphibians) and Yamazaki et al (1994; concerning mouse) reported zonases which appeared to be serine proteases. The biological and biochemical rationale behind two different types of zonases among hatching animals is at present not fully understood.

In Atlantic salmon, we have found the predominant zonases to be serine proteases. These are present in large amounts in the waste waters and hatching fluids of salmon eggs. In this crude aqueous state, salmon zonases may be effectively readied for purification by conventional techniques. This source of zonases offers a great advantage compared to isolation of enzymes from whole embryos, since it effectively obviates complications from extraneous biomaterial (eggshells, embryos and larvae). Thus, enzyme purification becomes greatly simplified.

An additional advantage is that the developmentally-staged salmon eggs may be transferred to minimal volumes of water prior to hatching. When highly synchronous hatching is induced by elevated (room) temperatures, or by deoxygenaton (Oppen-Berntsen et al. 1990), this yields a small volume of highly concentrated preparation of crude zonases.

A further essential aspect of this procedure is that, despite the increasing concentration of the proteolytic zonases, the stability of its resident zonases was observed to remain intact. Furthermore, it is important to note that this procedure yields zonase enzymes in a medium of almost pure water, containing at most 1 mM NaCl, but where zonases nevertheless possess and retain full enzymatic integrity over time. This preparation is therefore a valuable starting material for subsequent preparations of proteolytic zonases in various degree of purification, up to sequence-grade purity.

EXAMPLE 1

Concentrated Preparation of Crude Zonase from Atlantic Salmon

The initial purification of zonases involves only filtration of hatched salmon eggs through cheese cloth. Such a filtrate may be frozen for years without significant zonase degradation, before being thawed and employed for further zonase purification. This fact greatly simplifies production of a starting material for purifying salmon zonases.

The next step involves adjusting the "zonase crude" to usually 4 M urea, which dissociates fragments of the salmon eggshell and allow their removal along with extraneous debris by low speed configuration (15,000 g; 2×15 min). This material shows no sign of clogging columns, which is characteristic of crude materials prepared differently from what is described above. A "zonase crude" preparation suitable for purification by conventional chromatographic techniques is thus available. It is noteworthy that the salmon zonases are stable and catalytically active in 4, or even 8 M urea. Furthermore, this preparation of salmon zonase is effectively inhibited only by inhibitors of serine protease-type of proteases.

EXAMPLE 2

Purified Zonases from Atlantic Salmon

The product extracted from the "zonase crude" preparation may be chosen in different stages of purification. However, already after one round of gel filtration, zonases are separated from the larger molecular components in the filtrate with a 12 fold purification with better than a 50% yield. Larger components present in the "zonase crude" seem for the most part to be soluble fragments of the eggshell, to which some zonases are bound tightly. It is essential that the high molecular weight contaminants are discarded at this early stage of purification, as their presence will otherwise interfere with, and block, the success of subsequent purification steps. In other words, the sequence in which the conventional purification methods are undertaken, is an essential aspect of the process.

The matrix utilized may vary, but SEPHACRYL SR-200 is our usual choice. The buffer was Tris-HCl pH 8.0 or pH 8.5 (0.05 M) or Tris-Acetate (0.025 M, same pHs). The zonases obtained after gel filtration procedures account for the predominant zonase moieties in the "zonase crude", and the enzymatic activity was catalytically inhibited by benzamidine.

In terms of proteins, the zonases account for about 10% of the material already at this stage. This partly purified salmon zonase is again only inhibited by serine protease-type inhibitors.

EXAMPLE 3

Zonase as a Homogeneous Protein Product

Due to zonase inhibition by benzamidine, the enzyme fractions retarded on gel filtration columns, may be readily purified further by affinity chromatography on commercially available Benzamidine SEPHAROSE 6B-columns. This steps allows a 7.5 fold purification for an overall 94 fold total purification over the "zonase crude", with a yield of 37% of activity.

The specific conditions utilized (with columns of 25 or 125 ml volumes) was again a 0.05 M Tris-HCl buffer (pH 8 or 8.5), which for removing non-specifically bound material on the columns, was adjusted to 1 M NaCl. Zonases are not removed by this step, as they remain tightly bound to the column. The success of this step is critically due to elution of zonases from the column using a 10–33% dioxane-gradient in 1 M NaCl in the same Tris-HCl buffer. This procedure hinges on the unusual stability of salmon zonases in organic solvents.

After affinity-purification, the zonase preparation exhibits one protein band on SDS-PAGE analysis, with a molecular weight of around 28 kDa. This moiety of zonase was strongly antigenic, allowing production of polyclonal antibodies which specifically recognize salmon zonases, but not other salmon serine proteases such as salmon trypsins. Conversely, polyclonal antibodies to salmon trypsins do not recognize salmon zonases, establishing salmon zonase as a distinct product of embryonic salmon. However, this zonase product is not of sequence-grade purity, as revealed by Edman procedures for its N-terminal sequence. However, beyond the initial dozen N-terminal steps of sequencing, the overall amino acid sequence of this protein was shown to be similar to pure zonases. This highly purified salmon zonase preparation is also specifically inhibited only by serine protease-type inhibitors.

EXAMPLE 4

Zonase Prepared with Sequence-Grade Purity

Gelfiltration-purified plus affinity-purified salmon zonases may be further purified to sequence-grade purity by one final chromatographic procedure. This procedure employs a PBE94 column, with a buffer of Tris-Acetate (10 mM, pH 9.0), where subsequent elution was with a salt gradient (up to 1 M NaCl salt) in this buffer. This step itself increases the catalytic activity of the zonases by a further 7.6 fold, for an overall purification of 714 fold and with a yield of 28% from the starting material. This purification step leaves the protein identity of the zonases intact as a 28 kDa moiety. Hence, the step does not remove unrelated, major protein contaminants from the zonase preparation, as is customary for protein purification, as also illustrated in Examples 2 & 3. The molecular weight of purified zonases is the same as observed by Western blotting technique for zonase moieties present in the hatching fluid and in the "zonase crude".

What apparently takes place in the third and final chromatographic procedure is that small, contaminating peptides are removed. These peptides appear to be oligopeptides with around a dozen residues, originating most likely from the eggshell and/or from the salmon embryo. These peptide contaminants appear to exert inhibitory effects on zonase catalysis, since their removal increases the catalytic activity of zonase. Also, their presence interferes with the first steps in the Edman-sequencing of this zonase product. The two forms of zonases seen in this third purification step bind somewhat differently to the column matrix. However, both forms have similar amino acid sequences in their N-terminal portions.

Partial amino acid sequences from CNBr-generated peptides established the zonases as a distinct proteins. Structural analysis yielded indications that zonases may have distinct catalytic and substrate-binding domains, which may account for their sensitivity to calcium-chelating agents when acting on macromolecular (physiological) substrates (binding to inhibited, hence catalysis is inhibited indirectly), and also sensitivity to serine protease-inhibitors when acting on small substrates (catalysis is directly inhibited).

EXAMPLE 5

Chemical Properties of Salmon Zonases

The catalytic action of zonases is unaffected by the presence of salt in molar concentration, being nearly as effective in destilled water as in 6M salt. The enzyme is essentially equally active between pH 7 and 9. However, zonase is inactivated below pH 4, and only weakly active at pH 6. Zonase is unaffected by the presence of 8 M urea. Zonase can be stored at room temperature (with and without urea) for fifty days with only minimal loss of enzymatic activity. Enzymatic activity is also not impeded by even 40% (v/v) of organic solvents such as dioxane or propanol. In contrast, the enzyme is easily inactivated by 10% (v/v) of 2-mercaptoethanol, which may subsequently be removed by evaporation at 50° C. Catalysis is maximal at 42° C. (using the commercial chromozym X ((from Boehringer), with little, but significant catalytic action observed above 65° C., or after heating to up to 90° C. for 5 min, and subsequently cooled and assayed at room temperature.

EXAMPLE 6

Catalytic Characteristics of Salmon Zonases

The salmon zonases in question will cleave a whole series of chromozym substrates, with a maximal avidity displayed for peptide bonds with basic amino acids (preferably arginine). With these small artificial substrates, the zonases are as active as other serine proteases, but the $K_M$=14 $\mu$M, is lower. The Vmax is equal to 1.3 $\mu$M/min, and the $Kcat/K_M$ of 57 (/mM sec, compared to a value of about 1 for bovine and porcine (cationic) trypsins. The high degree of specificity in terms of cleaving peptide bonds compared to other serine proteases such as trypsin, is shown by use of eggshell zr-proteins (See: Walther 1993) as substrate: Trypsin will cleave these proteins into many small fragments, while zonases are observed to hardly degrade what is its physiological substrate.

The observed specificity of salmon zonase action reflects of course exactly what is required of a zonase: Such enzymes must rapidly destroy the mechanical, but not the chemical integrity of the eggshell-proteins so that the embryo may exit from the egg. To do this in a rapid manner in the presence of extraordinary high amounts of the eggshell substrate, requires that only a minimal number of peptide-bonds are attacked specifically. However, upon prolonged exposure to its substrate, the zonases will eventually also split other peptide-bonds as well. This sequence-specificity n terms of proteolysis has been observed, but it has not as yet been delineated in chemical detail. Nevertheless, the zonases seem to possess excellent prospects in terms of accomplishing specific splits in various candidate proteins, as nowadays are achieved using commercial enzyme-preparations of enzymes possessing (other) site-specific properties, e.g. the Boehringer products Asp-N and Glu-C. Thus, zonases rank alongside commercial enzymes which have found use in analytical work preparatory to protein sequenation, by yielding defined peptides from the large proteins to be sequenced. Thus, this trait of the enzymology of pure salmon zonases is commercially valuable.

What is claimed is:

1. A method of obtaining a purified zonase from hatchery-produced salmon eggs, comprising:
   a) inducing synchronized and rapid hatching of salmon eggs suspended in a volume of water so as to obtain a hatching fluid containing the zonase;
   b) collecting and concentrating the hatching fluid so as to obtain a concentrated fluid product;
   c) purifying the concentrated fluid product to obtain a zonase crude material;
   d) treating the zonase crude material by addition of solid urea to a concentration of one of 2M, 4M, and 8M to obtain a mixture; and subjecting the mixture to low speed centrifugation to remove fragments along with extraneous debris and obtain an extract; and
   e) further purifying the extract by carrying out the following sequential steps:
      subjecting the extract to gel filtration to obtain an enzyme fraction;
      purifying the enzyme fraction by affinity chromatography in a column;
      eluting zonase from the column with an organic solvent comprising a 10–33% dioxane gradient in a concentrated salt solution to obtain an eluate; and
      subjecting the eluate to ion-exchange chromatography to obtain a purified salmon zonase.

* * * * *